(12) United States Patent
Fallouh

(10) Patent No.: US 12,138,109 B2
(45) Date of Patent: *Nov. 12, 2024

(54) DEVICE AND METHOD FOR DIAGNOSIS OF CARDIAC TAMPONADE

(71) Applicant: Hazem Fallouh, Stonnal (GB)

(72) Inventor: Hazem Fallouh, Stonnal (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/822,187

(22) Filed: Aug. 25, 2022

(65) Prior Publication Data

US 2022/0401061 A1 Dec. 22, 2022

Related U.S. Application Data

(63) Continuation of application No. 16/762,290, filed as application No. PCT/EP2018/080629 on Nov. 8, 2018, now Pat. No. 11,471,122.

(30) Foreign Application Priority Data

Nov. 8, 2017 (GB) .................................... 1718458

(51) Int. Cl.
*A61B 8/06* (2006.01)
*A61B 5/00* (2006.01)
(Continued)

(52) U.S. Cl.
CPC .......... *A61B 8/065* (2013.01); *A61B 5/02035* (2013.01); *A61B 5/0215* (2013.01);
(Continued)

(58) Field of Classification Search
CPC ... A61B 8/065; A61B 5/02035; A61B 5/0215; A61B 5/0285; A61B 5/029;
(Continued)

(56) References Cited

U.S. PATENT DOCUMENTS

| 6,193,680 B1 * | 2/2001 | Parsons ............... A61M 60/468 601/149 |
| 7,883,500 B2 | 2/2011 | Levin et al. |

(Continued)

FOREIGN PATENT DOCUMENTS

| JP | 2006518249 A | 8/2006 |
| KR | 101517071 | 5/2015 |
| WO | 2004066817 A2 | 8/2004 |

OTHER PUBLICATIONS

Cogswell, TL et al., "The shift in the relationship between intrapericardial fluid pressure and volume induced by acute left ventricular pressure overload during cardiac tamponade.", Circulation Jul. 1986, vol. 74, No. 1, Jul. 1986 (Jul. 1986), pp. 173-180.

(Continued)

*Primary Examiner* — Rochelle D Turchen
(74) *Attorney, Agent, or Firm* — Greenberg Traurig, LLP; David J. Dykeman; Roman Fayerberg

(57) ABSTRACT

The invention relates to a system for challenging the pericardial space, to provide an indication of the risk of cardiac tamponade in a patient, as well as methods for diagnosis of, and determination of the extent of, a tamponade, and treating a patient in whom there is a detected cardiac tamponade.

20 Claims, 4 Drawing Sheets

(51) Int. Cl.
  *A61B 5/02* (2006.01)
  *A61B 5/0215* (2006.01)
  *A61B 5/0285* (2006.01)
  *A61B 5/029* (2006.01)
  *A61B 8/00* (2006.01)
  *A61B 8/08* (2006.01)
  *A61B 8/12* (2006.01)

(52) U.S. Cl.
  CPC ............ *A61B 5/0285* (2013.01); *A61B 5/029* (2013.01); *A61B 5/6853* (2013.01); *A61B 5/7275* (2013.01); *A61B 8/12* (2013.01); *A61B 8/445* (2013.01); *A61B 8/488* (2013.01); *A61B 2562/0247* (2013.01)

(58) Field of Classification Search
  CPC ....... A61B 5/6853; A61B 5/7275; A61B 8/12; A61B 8/445; A61B 8/488; A61B 2562/0247
  See application file for complete search history.

(56) References Cited

U.S. PATENT DOCUMENTS

| | | |
|---|---|---|
| 2004/0254483 A1 | 12/2004 | Zdeblick |
| 2005/0283092 A1 | 12/2005 | Gedebou |
| 2009/0177090 A1 | 7/2009 | Grunwald et al. |
| 2015/0032007 A1 | 1/2015 | Ottevanger et al. |
| 2015/0080875 A1* | 3/2015 | Kasprzyk ........... A61B 18/1815 606/33 |
| 2017/0258521 A1 | 9/2017 | Asirvatham et al. |
| 2020/0352540 A1 | 11/2020 | Fallouh |
| 2021/0196228 A1* | 7/2021 | Raju ..................... A61B 8/466 |

OTHER PUBLICATIONS

Segal, J., et al., "Continuous determination of cardiac output using a flow-directed doppler pulmonary artery catheter", Journal of Cardiothoracic and Vascular Anesthesia, Saunders, vol. 5, No. 4, Aug. 1, 1991, pp. 309-315.

Sharp, JT et al., "Hemodynamics during induced cardiac tamponade in man", American Journal of Medicine, Excerpta Medica, Inc., vol. 29, No. 4, Oct. 1, 1960, pp. 640-646.

International Search Report in PCT International Application No. PCT/EP2018080629 mailed Apr. 12, 2019.

* cited by examiner

DEVICE AND METHOD FOR DIAGNOSIS OF CARDIAC TAMPONADE

CROSS-REFERENCE TO RELATED APPLICATIONS

This application is a continuation application of U.S. patent application Ser. No. 16/762,290, filed on May 7, 2020, which is the U.S. national stage patent application of International Patent Application No. PCT/EP2018/080629, filed on Nov. 8, 2018, which claims priority to and the benefit of U.K. Patent Application No. 1718458.1, filed Nov. 8, 2017, which applications are incorporated herein by reference in their entireties.

FIELD

The present invention relates to a system and method for monitoring cardiac output in a patient, in particular in assessment of cardiac tamponade.

BACKGROUND

Cardiac surgery patients require post-operative intensive care management routinely for at least 24 hours. Major systems functions are monitored vigorously in order to diagnose early signs of certain organ failure. Respiratory, renal, neurological, and most importantly cardiac function and fluid management are among the systems monitored.

In order to monitor cardiac function invasive monitoring devices and tools are used, including central venous pressure lines, arterial pressure lines, pulmonary artery catheters and other devices like the trans oesophageal Doppler or Lithium dilution methods. These devices offer parameters that can help in assessing the cardiac function and status of the fluid balance in the patient to various degrees of accuracy. However, the devices that offer the most accurate and reproducible information about cardiac function and fluid management tend to require a high level of expertise and are invasive. For example, the pulmonary artery catheter (Swan Ganz) is the most accurate tool to measure cardiac output but has a complication risk which has been reported to be in the region of 0.3% in adult patients, requires expertise for insertion, and in up to 10-20% of the cases can fail to give meaningful parameters (due to failure to wedge as an example). The trans-oesophageal Doppler requires a probe to be inserted in the oesophagus and can give valuable information about the trend in cardiac output by measuring flow by detecting the Doppler signal in the descending aorta. The problem is the need to insert a separate probe in the oesophagus and the consistency of the measurement is very much dependent on positioning and requires continuous adjustment. Additionally, its use in paediatrics is limited due to the small size of the patient's mouth and oesophagus.

An additional limitation in perioperative cardiac monitoring is in diagnosing a perioperative complication known as cardiac tamponade. This condition is caused by the external compression of blood clots preventing cardiac relaxation. The condition can be difficult to diagnose as it can often be confused with another common condition in which the heart muscle fails to contract rather than relax. While the latter condition needs to be managed with inotropic support, cardiac tamponade requires emergency surgery. Reopening the chest following cardiac surgery can be lifesaving when done at the appropriate time, but unnecessary or delayed chest opening have both clinical and logistical implications. Reopening the chest tends to happen most frequently during the night and may cause staffing issues as these surgeries require highly experienced staff and surgeons. The surgery also increases the risk of the patient developing sepsis and delays recovery. This may explain some of the reluctance in opening the chest early in some cases, but reopening the chest when the situation develops into a much worse case has limited success. Thus, surgeons often have to decide whether reopening the chest will be beneficial to the patient, knowing that if left too late the patient will most likely die, with limited ability to accurately diagnose the problem.

The present invention addresses the need for accurate identification of cardiac tamponade.

US2005/0283092 discloses a medical device for the prevention or treatment of compartment syndrome, in which the pressure developed within a compartment impacts upon a balloon residing in a compartment, such that a dangerous level of pressure creates an alert. The pericardium space is not deliberately challenged, and the alert allows for responsive action only.

STATEMENTS OF INVENTION

A system for assessing the extent of cardiac tamponade in a patient, comprising:
  a Doppler probe capable of detecting velocity and/or flow of blood in either the left or right ventricular outflow tract;
  a balloon suitable for insertion and inflation in the pericardial space, mediastinal space, behind the sternum, or behind the heart; and
  a processing device communicatively coupled to the probe and optionally also the balloon
  wherein the processing device is configured for determination of blood flow through the left or right ventricular outflow tract, such that the system gives an indication of the extent of potential tamponade in the patient based on the relationship between the volume of inflation of the pericardial balloon and the blood flow through the left or right ventricular outflow tract.

A balloon suitable for placement in the pericardial space, mediastinal space, behind the sternum, or behind the heart, configured to provide substantially even pressure across the heart when inflated, and with a volume variable from 1 ml to 250 ml.

A Doppler probe suitable for placement on the pulmonary artery bifurcation of the heart, the probe communicatively coupled to a processing device, wherein the processing device is configured for calculation of blood flow through the pulmonary artery. In another embodiment, the probe is suitable for placement under the aortic arch of the heart, the probe communicatively coupled to a processing device, wherein the processing device is configured for calculation of blood flow through the aorta or left ventricular outflow tract. In a separate embodiment the probe is suitable for both placements.

A method for detecting cardiac tamponade comprising
  (1) inflating a balloon located in the pericardial space, mediastinal space, behind the sternum, or behind the heart;
  (2) measuring the velocity and/or flow of blood through the left or right ventricular outflow tract, suitably using a Doppler probe, wherein the probe is communicatively coupled to a processor,
  (3) wherein the processor is configured for calculation of blood flow through the left or right ventricular outflow tract such that the system gives an indication of the extent of potential tamponade in the patient based on the relationship between the volume of inflation of the pericardial balloon and the blood flow through the left or right ventricular outflow tract.

A system for challenging the pericardial space, to provide an indication of the risk of cardiac tamponade in a patient, comprising:
  a probe, suitably a Doppler probe, capable of detecting velocity and/or flow of blood in either the left or right ventricular outflow tract;
  a balloon suitable for insertion and inflation in the pericardial space, mediastinal space, behind the sternum, or behind the heart; and
  a processing device communicatively coupled to the probe and optionally also the balloon
  wherein the processing device is configured for determination of blood flow through the left or right ventricular outflow tract, such that the system gives an indication of the extent of potential tamponade in the patient based on the relationship between the volume of inflation of the pericardial balloon and the blood flow through the left or right outflow tract
  wherein the inflation of the balloon may be or is carried out to such an extent that the blood flow through the left of right ventricular outflow tract is impacted.

The system allows identification of the patients who are at risk of developing clinically significant tamponade due to the progressive reduction in the value of such volume.

A method for diagnosing the presence of, and/or detecting the extent of, a cardiac tamponade in an individual, the method comprising inflating a balloon located in one of the pericardial space, the mediastinal space, behind the sternum, or behind the heart, to such an extent that the velocity and/or flow of blood through the left or right ventricular outflow tract changes, optionally as measured by a Doppler probe, thereby providing an indication of any potential tamponade or the extent of any tamponade. Optionally the velocity or flow of blood is measured by a probe that is communicatively coupled to a processor, the processor configured for calculation of blood flow through the left or right ventricular outflow tract.

A method for diagnosing the presence of, or detecting the extent of a cardiac tamponade comprising
  (1) inflating a balloon located in the pericardial space, mediastinal space, behind the sternum, or behind the heart;
  (2) measuring the velocity and/or flow of blood through the left or right ventricular outflow tract using a probe, suitably using a Doppler probe, wherein the probe is communicatively coupled to a processor,
  (3) wherein the processor is configured for calculation of blood flow through the left or right ventricular outflow tract
  wherein the balloon is inflated to such an extent that the blood flow through the left or right ventricular outflow tract is affected,
  such that the system gives an indication of the extent of potential tamponade in the patient based on the relationship between the volume of inflation of the balloon and the blood flow through the left or right ventricular outflow tract.

A method for treating cardiac tamponade, the method comprising
  determining the space available within the any of the pericardial space, the mediastinal space, behind the sternum, or behind the heart by inflating a balloon located in the pericardial space, the mediastinal space, behind the sternum, or behind the heart, respectively, to such an extent that the velocity and/or flow of blood through the left or right ventricular outflow tract changes, optionally as measured by a Doppler probe, thereby providing an indication of any potential tamponade, and subsequent removal of all or part of any obstruction within the pericardial space, the mediastinal space, behind the sternum, or behind the heart in the event that the inflation of the balloon is consistent with cardiac tamponade being detected. Optionally the velocity or flow of blood is measured by a probe that is communicatively coupled to a processor, the processor configured for calculation of blood flow through the left or right ventricular outflow tract.

A method for treating cardiac tamponade comprising
  (1) inflating a balloon located in the pericardial space, mediastinal space, behind the sternum, or behind the heart;
  (2) measuring the velocity and/or flow of blood through the left or right ventricular outflow tract using a probe, suitably using a Doppler probe, wherein the probe is communicatively coupled to a processor,
  (3) wherein the processor is configured for calculation of blood flow through the left or right ventricular outflow tract
  wherein the balloon is inflated to such an extent that the blood flow through the left or right ventricular outflow tract is affected,
  such that the system gives an indication of the extent of potential tamponade in the patient based on the relationship between the volume of inflation of the balloon, eg and the blood flow through the left or right ventricular outflow tract or cardiac output,
  and treating the tamponade

DETAILED DESCRIPTION OF THE INVENTION

The present invention provides a system comprising a probe, suitably easy to insert during surgery and placed during surgery on the aorta or the pulmonary artery bifurcation under the aortic arch. The probe allows monitoring of velocity of blood by measuring a Doppler signal of the velocity of the blood cells in the left or right ventricular outflow tract respectively. The blood flow out of the heart can therefore be determined, and thus cardiac output may be calculated by multiplying the volume of blood flowing through the outflow tract (the stroke volume) by the patient's heart rate. In particular, the cardiac output variation can be determined in response to the inflation of an expandable balloon, inserted into the pericardial space, mediastinal space, behind the sternum, or behind the heart, which can be inflated by, for example, a known volume of fluid. Inflation of the balloon creates an artificial tamponade and will at some point impact the ability of the heart to pump blood and therefore impact blood flow in the left or right ventricular outflow tract. The less the balloon needs to be inflated to impact the blood flow in the outflow tract, the greater the degree of existing tamponade.

Therefore, balloon inflation in conjunction with blood flow determination can be used to diagnose cardiac tamponade, as measured by blood flow through the left or right ventricular outflow tract detected by Doppler analysis. The blood flow can be determined by a processor in communication with the probe used to detect flow.

The invention thus relates both to a system to monitor the cardiac output, diagnose cardiac tamponade, and further to a method for identification of a person having cardiac tamponade, in particular to identification of a patient in need of surgery to address cardiac tamponade (i.e. reopening the chest to relieve pressure).

In particular the invention relates to methods and systems for actively challenging the space around the heart, rather than by passive monitoring. The space may be challenged until an effect on heart performance is detected, to allow a suitable treatment plan to be implemented.

In the present invention the space within the pericardium, for example, is assessed by inflation of a balloon to such an extent that the space is challenged by the balloon, such that at a certain point the activity of the heart is then impacted, for example as determined by the blood flow measured by a Doppler probe. In this way the likelihood of an adverse event caused by tamponade can be assessed and even prevented without the need to be reactive to an acute event.

Additionally the invention offers a level of predictability by monitoring the volume that is required to cause significant tamponade effect, which can arise from a clot and bleeding or even from the swelling of the heart, particularly in the paediatric population. The invention therefore allows a physician to understand whether a patient is likely to benefit from opening the chest, and whether to keep the chest opened until the oedema is reduced in a day or two, or close it immediately.

The present invention will not only allow determination of whether there is a physiological sign of tamponade, which can be present but well tolerated, but also to assess the impact of adding a known challenge (eg a known inflation volume into the pericardium) on the haemodynamics of the patient, and thereby informing the clinician of the relationship (and trend) between volume added and the level of compromise in the function of the heart. This can be due to ongoing bleeding or progressive oedema in the myocardium. As mentioned above, such information will enable the surgeon to plan any reopening of the chest needed and predict its need.

Equally, observing the trend of a reduction in the volume required to induce a nominated level of haemodynamic instability as a result of tamponade is an indicator of the progressive nature of the clinical condition and therefore predict the need for the time for treatment, such as re-opening the chest.

The invention allows identification of patients who are at risk of developing clinically significant tamponade, those in whom there is a progressive reduction in the value of the challenge volume needed to affect cardiac output.

This system and method disclosed herein can give a surgeon an indication of whether a patient will benefit from chest opening in the situation of poor cardiac output when an element of tamponade is suspected. Both conditions present the same way, but their treatment is different, and so the invention allows the optimal procedure to be then selected.

In one aspect the invention therefore provides a system for assessing the extent of cardiac tamponade in a patient, comprising:
- a Doppler probe capable of detecting velocity and/or flow of blood in either the left or right outflow tract;
- a balloon suitable for insertion and inflation in the pericardial space, mediastinal space, behind the sternum, or behind the heart; and
- a processing device communicatively coupled to the probe and optionally also the balloon wherein the processing device is configured for determination of blood flow through the left or right ventricular outflow tract, which is known as cardiac output. The system gives an indication of the extent of potential tamponade in the patient based on the relationship between the volume of inflation of the pericardial balloon the pressure of the balloon in response to certain volume and the blood flow through the left or right outflow tract. Such a system could also use measurement of variation of cardiac output from other cardiac output monitoring devices, such as and not limited to a pulmonary artery catheter or lithium dilution devices.

In another aspect the invention relates to a system for challenging the pericardial space, to provide an indication of the risk of cardiac tamponade in a patient, comprising:
- a probe, suitably a Doppler probe, capable of detecting velocity and/or flow of blood in either the left or right ventricular outflow tract;
- a balloon suitable for insertion and inflation in the pericardial space, mediastinal space, behind the sternum, or behind the heart; and
- a processing device communicatively coupled to the probe and optionally also the balloon wherein the processing device is configured for determination of blood flow through the left or right ventricular outflow tract, such that the system gives an indication of the extent of potential tamponade in the patient based on the relationship between the volume of inflation of the pericardial balloon and the blood flow through the left or right outflow tract, or cardiac output, wherein the inflation of the balloon may be or is carried out to such an extent that the blood flow through the left of right ventricular outflow tract is impacted.

In another aspect the invention relates to a method for diagnosing the presence of, and/or detecting the extent of, a cardiac tamponade in an individual, the method comprising inflating a balloon located in one of the pericardial space, the mediastinal space, behind the sternum, or behind the heart, to such an extent that the velocity and/or flow of blood through the left or right ventricular outflow tract changes, optionally as measured by a Doppler probe, thereby providing an indication of any potential tamponade or the extent of any tamponade. Optionally the velocity or flow of blood is measured by a probe that is communicatively coupled to a processor, the processor configured for calculation of blood flow through the left or right ventricular outflow tract.

In another aspect the invention relates to a method for diagnosing the presence of, or detecting the extent of a cardiac tamponade comprising
(1) inflating a balloon located in the pericardial space, mediastinal space, behind the sternum, or behind the heart;
(2) measuring the velocity and/or flow of blood through the left or right ventricular outflow tract using a probe, suitably using a Doppler probe, wherein the probe is communicatively coupled to a processor,
(3) wherein the processor is configured for calculation of blood flow through the left or right ventricular outflow tract
wherein the balloon is inflated to such an extent that the blood flow through the left or right ventricular outflow tract is affected,
such that the system gives an indication of the extent of potential tamponade in the patient based on the relationship between the volume of inflation of the balloon and the blood flow through the left or right ventricular outflow tract.

In another aspect the invention relates to a method for treating cardiac tamponade, the method comprising
determining the space available within the any of the pericardial space, the mediastinal space, behind the sternum, or behind the heart by inflating a balloon located in the pericardial space, the mediastinal space, behind the sternum, or behind the heart, respectively, to such an extent that the velocity and/or flow of blood through the left or right ventricular outflow tract changes, optionally as measured by a Doppler probe, thereby providing an indication of any potential tamponade, and subsequent removal of all or part of any obstruction within the pericardial space, the mediastinal space, behind the sternum, or behind the heart in the event that the inflation of the balloon is consistent with cardiac tamponade being detected.

Optionally the velocity or flow of blood is measured by a probe that is communicatively coupled to a processor, the processor configured for calculation of blood flow through the left or right ventricular outflow tract.

In another aspect the invention relates to a method for treating cardiac tamponade comprising (1) inflating a balloon located in the pericardial space, mediastinal space, behind the sternum, or behind the heart;

(2) measuring the velocity and/or flow of blood through the left or right ventricular outflow tract using a probe, suitably using a Doppler probe, wherein the probe is communicatively coupled to a processor, (3) wherein the processor is configured for calculation of blood flow through the left or right ventricular outflow tract wherein the balloon is inflated to such an extent that the blood flow through the left or right ventricular outflow tract is affected, such that the system gives an indication of the extent of potential tamponade in the patient based on the relationship between the volume of inflation of the balloon and the blood flow through the left or right ventricular outflow tract; and treating cardiac tamponade in patients diagnosed with cardiac tamponade.

There are a number of preferred aspects of the system and methods of the invention.

In a preferred aspect the probe is a Doppler probe positioned at the bifurcation of the pulmonary artery below the aortic arch, and capable of measuring the Doppler signal en face (face on) of the right ventricular outflow tract, for measurement of blood velocity.

The probe is preferably substantially facing the direction of flow. An example of a suitable placement is at the pulmonary artery bifurcation under the aortic arch to capture blood cell velocity in the right ventricular outflow tract. Another suitable placement is on the surface of the aortic arch in a manner able to capture the Doppler signal of the blood cells travelling in the left ventricular outflow tract.

The probe may be suitable for placement on the pulmonary artery bifurcation, and is preferably suitable to be able to measure the Doppler signal en face (face on) of the right ventricular outflow tract, for measurement of blood velocity. The probe may be capable of providing real time cardiac output by allowing calculation of the flow from the measurement of the right ventricular outflow tract diameter taken in the operating room, either by the surgeon or by trans oesophageal echo.

In a separate embodiment, the probe may be suitable for placement along the ascending aorta or the apex of the left ventricle, and is preferably suitable to be able to measure the Doppler signal en-face of the left ventricular outflow tract or the mitral valve, for measurement blood velocity. The probe may be capable of providing real time cardiac output by allowing calculation of the flow from the measurement of the left ventricular outflow tract diameter taken in the operating room, either by the surgeon or by trans oesophageal echo.

The left and right ventricular outflow tracts are portions of the left and right ventricles respectively through which blood passes before entering the greater arteries. The left outflow tract connects to the aorta and the right outflow tract connects to the pulmonary artery. Thus, measuring flow through the left or right ventricular outflow tracts is equivalent to measuring flow through the aorta or pulmonary artery.

Preferred probes are substantially flat and configured to sit in the narrow space between the main pulmonary artery and the aortic arch or near the apex of the left ventricle. Preferably a probe has rounded edges, free from angulation, to stop it from engaging with any body structure while being pulled out of the body, such as catching on vessels, other devices such as pacing wires or pressure lines or the body compartment wall.

Preferably the probe is flexible and suitably has the ability to bend and be rolled into a suitable housing while being pulled out from the body after surgery.

In one embodiment the balloon may be a pressure sensing balloon having integral or associated means to determine resistance to inflation, or the degree of inflation, such as an integral sensor capable of sensing the degree of balloon expansion. Such a sensor could supplement information from the flow sensor in order to assess the free space around the heart.

In one embodiment the balloon is suitable for placement in the pericardial space, mediastinal space, behind the sternum, or behind the heart. The balloon is suitably configured to provide even pressure across the heart when inflated, preferably with a volume variable from 1 ml to 250 ml. Balloons may be made of any material approved or suitable for use inside the human body, and should be sterile or resides in a sterile housing.

In one embodiment the system has a balloon configured to occupy some of the pericardial space, mediastinal space, the space behind the sternum, or the space behind the heart when inflated, limiting space for the heart and thus challenging the space available to the heart to relax, and therefore determine whether the heart is at risk of developing tamponade soon.

In one embodiment the system comprises a housing compartment(s) for the probe and/or balloon, wherein said housing compartment(s) facilitate removal and/or insertion of the balloon or probe into the chest cavity, suitably by providing a delivery or retrieval pathway through an incision in the chest wall. Preferably the housing is ergonomically designed and is pliable and/or tubular.

In one embodiment the system further comprises a fluid delivery means for inflation of the balloon with fluid. The fluid may be a liquid or gas, but is preferably a liquid, such as sterile saline.

In one embodiment the processing device is configured for determination of blood flow and/or blood velocity through the right ventricular outflow tract such that the system gives a measure of right ventricular output. In a separate embodiment the processing device is configured for determination of blood flow and/or blood velocity through the left ventricular outflow tract such that the system gives a measure of left ventricular output. In a separate embodiment the processing device is configured for determining blood flow and/or blood velocity through either outflow tract.

In one embodiment the processing device is additionally configured to monitor the pressure measured by the balloon and the volume of fluid injected into the balloon, and optionally to generate a pressure-volume curve over time.

The flow of blood or blood flow can be calculated from measurements of blood velocity by multiplying the velocity as determined by the Doppler probe by the cross sectional area of the outflow tract.

Alternatively, the stroke volume can be calculated by multiplying the velocity time integral of the trace of the Doppler flow profile by the valve orifice cross sectional area.

The diameter of the left or right ventricular outflow tract is measured by the surgeon during the initial surgery or via the use of transoesophageal echo.

The system, of the invention, or components thereof, such as the probe and the balloon components, may be (and may be configured to be) withdrawn through the skin, suitably at an appropriate point in any medical procedure, such as when a patient leaves a critical care unit.

In parallel the invention relates to A method for detecting cardiac tamponade comprising (1) inflating a balloon located in the pericardial space, mediastinal space, behind the sternum, or behind the heart;

(2) measuring the velocity and/or flow of blood through the left or right ventricular outflow tract, suitably using a Doppler probe, wherein the probe is communicatively coupled to a processor, (3) wherein the processor is configured for determination of blood flow through the left or right ventricular outflow tract such that the system gives an indication of the extent of potential tamponade in the patient based on the relationship between the volume of inflation of the balloon and the blood flow through the left or right ventricular outflow tract.

In any aspect of the invention, the processing device is configured for:

a. Determination of flow through the left or right ventricular outflow tract such that the system gives a measure of the left or right ventricular output respectively.

b. Measuring the pressure and/or volume of the balloon and generating a relationship curve between the pressure and/or the volume inside the balloon and variation over time.

c. Generating a relationship curve between the blood flow through the left or right ventricular outflow tract and the volume of the balloon, or the volume of fluid injected into the balloon, over time.

d. Optionally, calculating the probability of a patient developing cardiac tamponade from an algorithm based on previous data which correlates with cardiac tamponade syndrome.

In one aspect, a patient is diagnosed with cardiac tamponade requiring surgical intervention when blood flow through the left or right ventricular outflow tract is reduced by inflation of the balloon. In one aspect the volume of the balloon is such that, when fully inflated, it would not impact a normal heart (one without tamponade), but would only have an effect on a heart with tamponade.

In one aspect, a patient is determined not to have cardiac tamponade when the blood flow through the left or right ventricular outflow tract is not reduced by inflation of the balloon and therefore unnecessary surgical intervention is avoided.

In a related aspect, the invention also relates to the use of a probe located at a pulmonary artery bifurcation in measuring right ventricular output using an epicardial monitoring Doppler device, wherein the probe is inserted on the pulmonary artery bifurcation, such that blood flow is measured in an "en face" orientation.

In a related aspect, the invention also relates to the use of a probe located along the ascending aorta or the apex of the heart in measuring left ventricular output using an epicardial monitoring Doppler device, such that blood flow is measured in an "en face" orientation to the left ventricular outflow tract or the mitral valve.

The invention also relates to a method for determining the pressure in the pericardial space, mediastinal space, the space behind the sternum, or the space behind the heart by creating an artificial and transient tamponade, the method comprising inflating a balloon within the pericardial space, mediastinal space, behind the sternum, or behind the heart and directly or indirectly determining the resistance to the inflation of the balloon, such as via cardiac output from the heart, preferably the blood flow through the right ventricular outflow tract.

The invention also relates to a balloon suitable for placement in the pericardial space, mediastinal space, behind the sternum, or behind the heart, configured to provide even pressure across the heart when inflated, and with a volume variable from 1 ml to 250 ml. In alternative embodiments, the balloon has a volume variable from 1 to 200 ml, such as 1 to 150 ml, 1 to 100 ml, or 20 to 100 ml.

The invention also relates to a Doppler probe suitable for placement on the pulmonary artery bifurcation under the aortic arch, communicatively coupled to a processing device, wherein the processing device is configured for determination of pressure through the pulmonary artery.

The invention also relates to a Doppler probe suitable for placement along the ascending aorta or near the apex of the lung, communicatively coupled to a processing device, wherein the processing device is configured for determination of pressure through the aorta.

The processing device may be provided with a predetermined statistical distribution of decrease in blood flow vs probability of tamponade. The processing device may be configured for determination of stroke volume by multiplying the velocity time integral of the trace of the Doppler flow profile by the valve orifice cross sectional area. The processing device may additionally be configured for calculating the decrease in flow as a function of balloon volume.

In one embodiment, the processing device indicates the probability of tamponade requiring surgical intervention based on the rate of decrease of flow as the balloon volume increases.

Any of the features of the invention described herein may be used with any of the systems and methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains.

All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps Any part of this disclosure may be read in combination with any other part of the disclosure, unless otherwise apparent from the context.

All of the systems and/or methods disclosed and claimed herein can be made and executed without undue experimentation in light of the present disclosure. While the systems and methods of this invention have been described in terms of preferred embodiments, it will be apparent to those of skill in the art that variations may be applied to the systems and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention is illustrated in the attached figures, in which

PREFERRED STATEMENTS OF THE INVENTION INCLUDE

Figure 1:
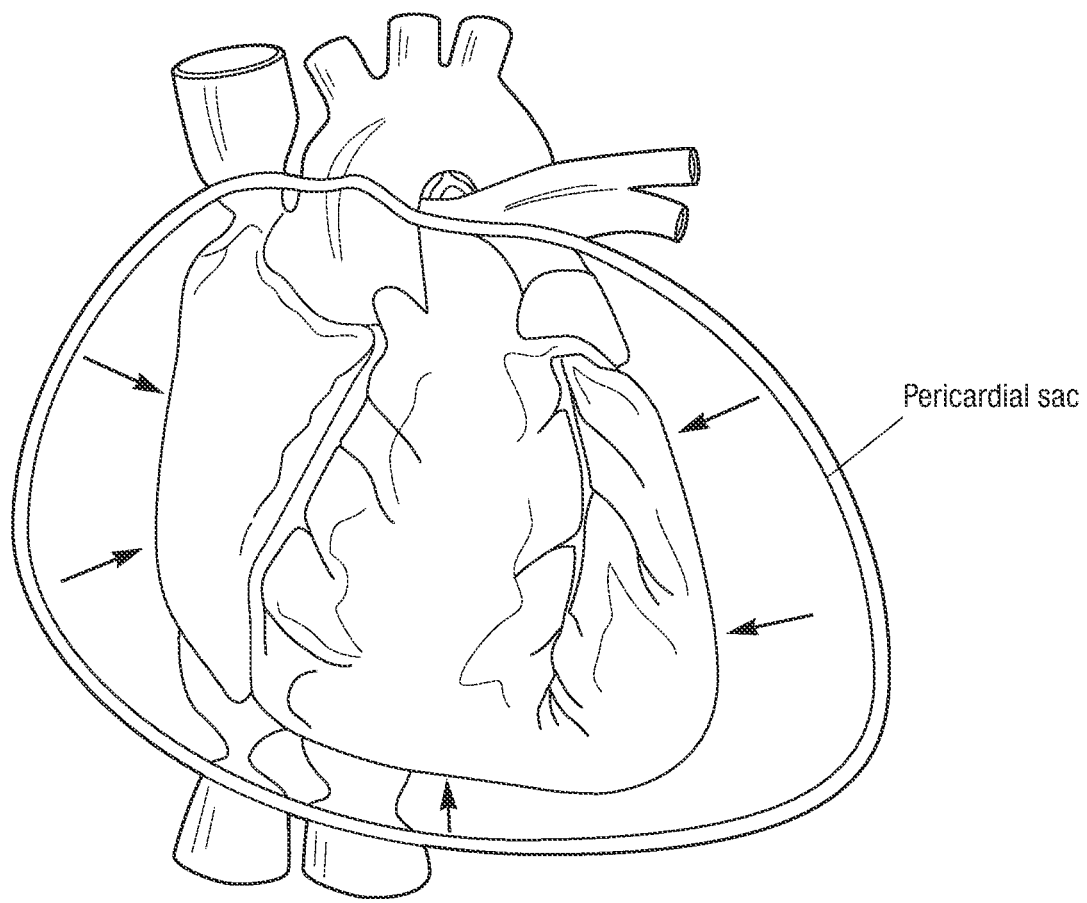
FIG. 1 shows the heart contained within the pericardial sac, with arrows demonstrating the pressure exerted on the heart during tamponade FIG. 2 also shows the heart contained within the pericardial sac. Compression of the heart following blood collection within the sac can be seen.
Figure 2:
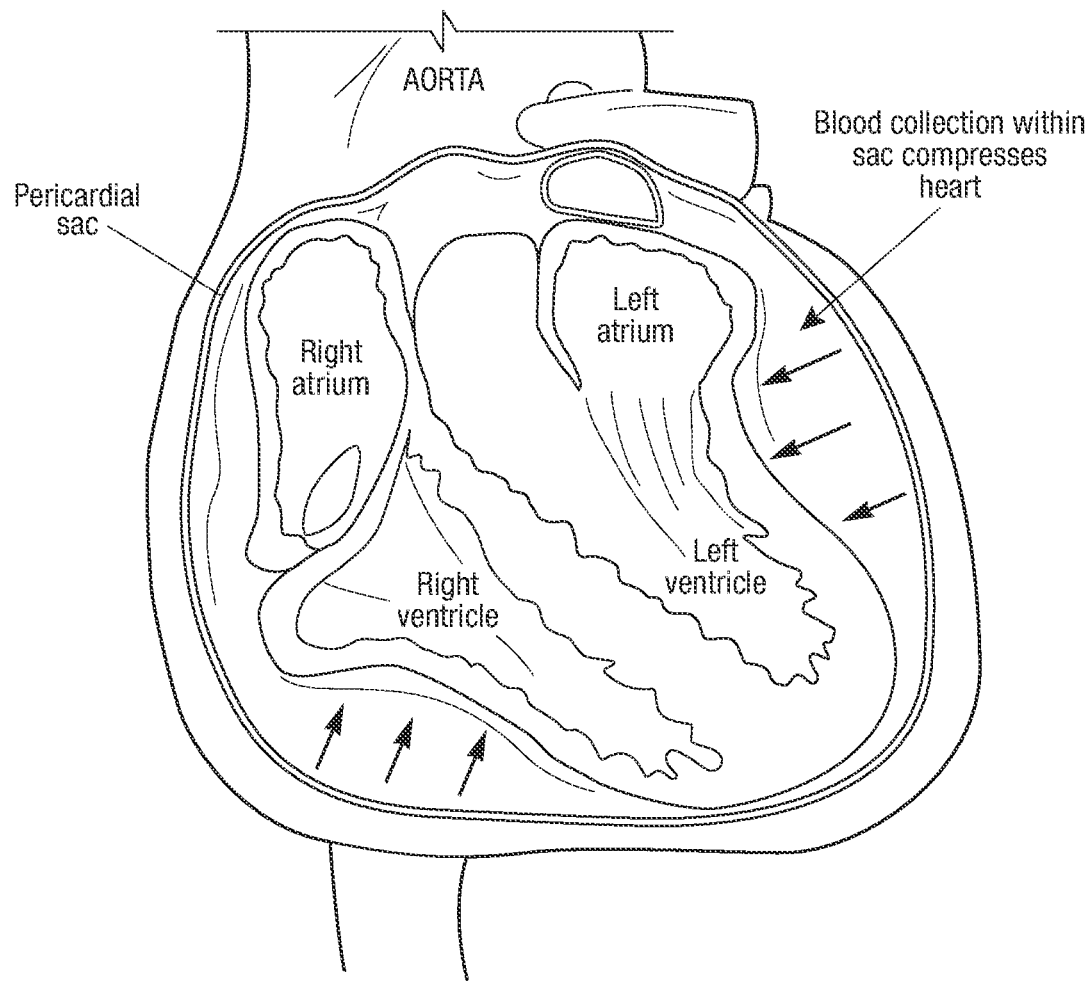
Figure 3:
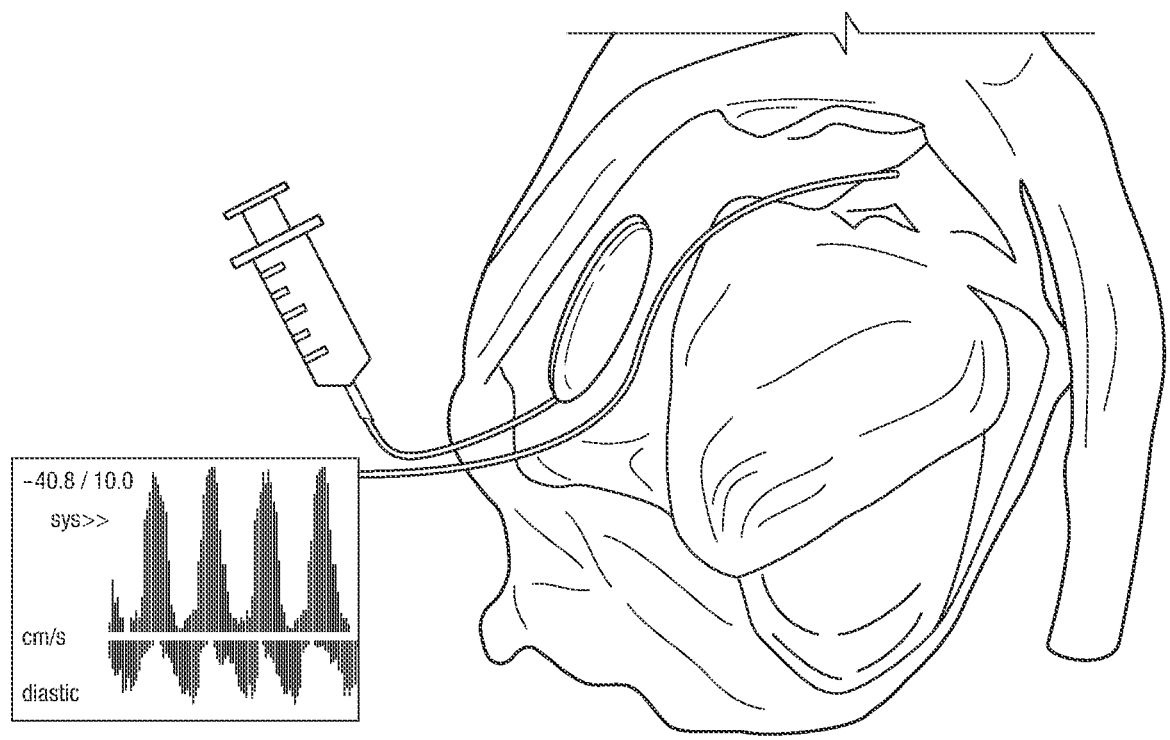
FIG. 3 is a diagram of one embodiment of the present invention. A balloon is inserted into the pericardial sac and injected with fluid, whilst a Doppler probe is suitably placed to monitor left or right ventricular outflow.
Figure 4:
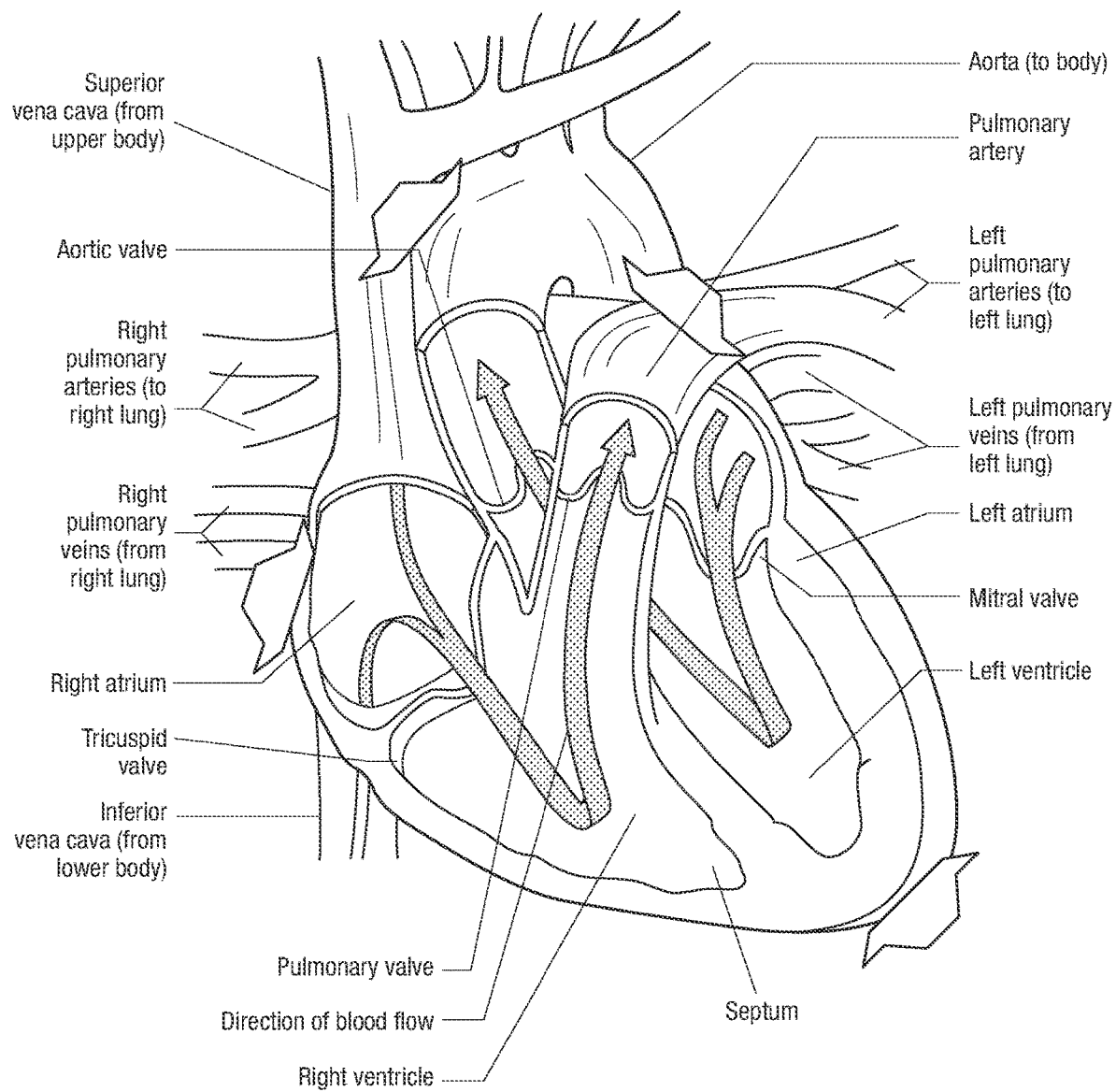
FIG. 4 is a diagram of the heart with major vessels labelled. The two preferred positions of the Doppler probe are indicated (on the aorta or on the pulmonary artery bifurcation).

1 A system for assessing the extent of cardiac tamponade in a patient, comprising:
A Doppler probe capable of detecting velocity and/or flow of blood in either the left or right ventricular outflow tract;
a balloon suitable for insertion and inflation in the pericardial space, mediastinal space, behind the sternum, or behind the heart; and
a processing device communicatively coupled to the probe and optionally also the balloon
wherein the processing device is configured for determination of blood flow through the left or right ventricular outflow tract, such that the system gives an indication of the extent of potential tamponade in the patient based on the relationship between the volume of inflation of the pericardial balloon and the blood flow through the left or right outflow tract.

2 The system of statement 1 wherein the balloon is a pressure-sensing balloon.

3 The system of any of statements 1-2 wherein the balloon is configured to provide even pressure over the heart when inflated.

4 The system of any of statements 1-3 wherein the balloon is configured to occupy some of the pericardial space, mediastinal space, the space behind the sternum, or the space behind the heart when inflated, limiting space for the heart and thus challenging the space available to the heart to relax and therefore determine whether the heart is at risk of developing tamponade.

5 The system of any of statements 1-4 further comprising housing compartment(s) for the probe and/or balloon, wherein said housing compartment(s) facilitate removal and/or insertion of the balloon into the chest, by providing a delivery pathway into the chest.

6 The system of statement 2 wherein the processing device is additionally configured to monitor the pressure sensed by the balloon and the volume of fluid injected into the balloon, and optionally to generate a pressure-volume curve over time.

7 The system of any preceding statements wherein the diameter of the left or right ventricular outflow tract is used to calculate flow from the measured blood velocity.

8 A balloon suitable for placement in the pericardial space, mediastinal space, behind the sternum, or behind the heart, configured to provide even pressure across the heart when inflated, and with a volume variable from 10 ml to 250 ml.

9 A method for detecting cardiac tamponade comprising
(1) inflating a balloon located in the pericardial space, mediastinal space, behind the sternum, or behind the heart;
(2) measuring the velocity and/or flow of blood through the left or right ventricular outflow tract, suitably using a Doppler probe, wherein the probe is communicatively coupled to a processor,
(3) wherein the processor is configured for calculation of blood flow through the left or right ventricular outflow tract such that the system gives an indication of the extent of potential tamponade in the patient based on the relationship between the volume of inflation of the balloon and the blood flow through the left or right ventricular outflow tract.

10 A method for diagnosing cardiac tamponade comprising
(1) inflating a balloon located in the pericardial space, mediastinal space, behind the sternum, or behind the heart;
(2) measuring the velocity and/or flow of blood through the left or right ventricular outflow tract, suitably using a Doppler probe, wherein the probe is communicatively coupled to a processor,
(3) wherein the processor is configured for calculation of blood flow through the left or right ventricular outflow tract such that the system gives an indication of the extent of potential tamponade in the patient based on the relationship between the volume of inflation of the balloon and the blood flow through the left or right ventricular outflow tract; and optionally
treating cardiac tamponade in patients diagnosed with cardiac tamponade.

The invention claimed is:
1. A system, comprising:
a probe, wherein the probe is configured to measure one or both of a velocity or a flow of blood through a left or right ventricular outflow tract;
a balloon, wherein the balloon is configured to change the velocity or the flow of blood through the left or right ventricular outflow tract upon inflation; and a processing device communicatively coupled to the probe and the balloon, wherein the processing device is configured to calculate blood flow through the left or right ventricular outflow tract when the balloon is in a pericardial space or in a mediastinal space, wherein
an indication of a cardiac tamponade in a patient is provided based on a relationship between a volume of inflation of the balloon and the blood flow through the left or right ventricular outflow tract.

2. The system of claim 1, wherein the balloon is further configured to:
be inflated up to a volume of at least 100 ml in the pericardial space or the mediastinal space.

3. The system of claim 1, wherein the probe is configured to be positioned on an outer surface of the left or right ventricular outflow tract such that the probe measures one or both of the velocity or flow of blood through the left or right ventricular outflow tract, respectively.

4. The system of claim 1, wherein the balloon is a pressure sensing balloon configured to determine resistance to inflation, or a degree of inflation of the balloon.

5. The system of claim 4, wherein the balloon comprises an integral sensor capable of sensing the degree of inflation of the balloon.

6. A system, comprising:
a probe, wherein the probe is configured to measure one or both of a velocity or a flow of blood through a left or right ventricular outflow tract;
a balloon, wherein the balloon is configured to change the velocity or the flow of blood through the left or right ventricular outflow tract upon inflation; and
a processing device communicatively coupled to the probe and the balloon, wherein the processing device is configured to:
calculate blood flow through the left or right ventricular outflow tract when the balloon is in a pericardial space or in a mediastinal space;
generate a relationship curve between the blood flow through the left or right ventricular outflow tract and a volume of inflation of the balloon; and
calculate a probability of a patient developing a cardiac tamponade based on the relationship curve and an algorithm based on previous data correlating with cardiac tamponade syndrome.

7. The system of claim 6, wherein the probe is configured to be positioned on an outer surface of the left or right ventricular outflow tract such that the probe measures one or both of the velocity or flow of blood through the left or right ventricular outflow tract, respectively.

8. The system of claim 6, wherein:
the balloon is a pressure sensing balloon; and
the processing device is further configured to:
monitor a pressure measured by the balloon and a volume of fluid injected into the balloon; and
generate a relationship curve between the pressure measured by the balloon and the volume of fluid injected into the balloon over time.

9. The system of claim 6, wherein the processing device is further configured to:
measure the volume of the balloon; and
generate a relationship curve between the volume of the balloon and a variation of cardiac output over time.

10. The system of claim 6, wherein the processing device is configured to calculate the blood flow through the left or right ventricular outflow tract by multiplying a velocity of blood flow, as determined by the probe, by a cross sectional area of the left or right ventricular outflow tract.

11. A system, comprising:
a probe, wherein the probe is configured to measure one or both of a velocity or a flow of blood through a left or right ventricular outflow tract;
a balloon, wherein the balloon is configured to change the velocity or the flow of blood through the left or right ventricular outflow tract upon inflation in a pericardial space or in a mediastinal space; and
a processing device communicatively coupled to the probe and the balloon, wherein the processing device is configured to receive data on blood flow through the left or right ventricular outflow tract when the balloon is in the pericardial space or in the mediastinal space, wherein
a probability of a cardiac tamponade in a patient is provided based on a relationship between a volume of inflation of the balloon and the blood flow through the left or right ventricular outflow tract using an algorithm based on previous data which correlates with cardiac tamponade syndrome.

12. The system of claim 11, wherein the probe is configured to be positioned on an outer surface of the left or right ventricular outflow tract such that the probe measures one or both of the velocity or flow of blood through the left or right ventricular outflow tract, respectively.

13. The system of claim 11, wherein the balloon is a pressure sensing balloon configured to determine resistance to inflation, or a degree of inflation of the balloon.

14. The system of claim 13, wherein the balloon comprises an integral sensor capable of sensing the degree of inflation of the balloon.

15. The system of claim 11, wherein the processing device is configured to calculate the blood flow through the left or right ventricular outflow tract by multiplying a velocity of blood flow, as determined by the probe, by a cross sectional area of the left or right ventricular outflow tract.

16. The system of claim 11, wherein the balloon is further configured to be inflated from a volume of 1 ml up to a volume of 250 ml in the pericardial space or the mediastinal space.

17. The system of claim 11, wherein the balloon is further configured to be inflated from a volume of 1 ml up to a volume of 200 ml in the pericardial space or the mediastinal space.

18. The system of claim 11, wherein the balloon is further configured to be inflated from a volume of 1 ml up to a volume of 150 ml in the pericardial space or the mediastinal space.

19. The system of claim 11, wherein the balloon is further configured to be inflated from a volume of 1 ml up to a volume of 100 ml in the pericardial space or the mediastinal space.

20. The system of claim 11, wherein the balloon is further configured to be inflated from a volume of 20 ml up to a volume of 100 ml in the pericardial space or the mediastinal space.

* * * * *